(12) United States Patent
Lifshitz

(10) Patent No.: US 6,350,241 B1
(45) Date of Patent: Feb. 26, 2002

(54) METHOD AND APPARATUS FOR MULTIPLE ANGLE COMPOUND FLOW IMAGING

(75) Inventor: Ilan Lifshitz, Tel-Aviv (IL)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/472,540

(22) Filed: Dec. 27, 1999

(51) Int. Cl.[7] ................................................. A61B 8/12
(52) U.S. Cl. ....................................................... 600/454
(58) Field of Search ................................ 600/437, 440, 600/441–447, 453–456, 463, 465, 419; 324/306; 73/861.25

(56) References Cited

U.S. PATENT DOCUMENTS

| | | | | |
|---|---|---|---|---|
| 4,937,797 A | * | 6/1990 | Snyder et al. ............... | 367/138 |
| 5,394,874 A | * | 3/1995 | Forestieri et al. ........... | 600/441 |
| 5,454,372 A | * | 10/1995 | Banjanin et al. ............ | 600/454 |
| 5,910,119 A | * | 6/1999 | Lin .............................. | 600/455 |
| 5,931,788 A | * | 8/1999 | Keen et al. .................. | 600/462 |
| 6,066,099 A | * | 5/2000 | Thomenius et al. ........ | 600/447 |

* cited by examiner

Primary Examiner—Marvin M. Lateef
Assistant Examiner—Ali M. Imam
(74) Attorney, Agent, or Firm—McAndrews, Held & Malloy, Ltd.; Peter J. Vogel; Michael A. Dellapenna

(57) ABSTRACT

A method for multi-angle compound flow imaging includes the steps of receiving first and second (in general, N) ultrasound signal reflections from a target. Each ultrasound signal reflection is preferably oriented at a different angle. The method further includes evaluating a display decision algorithm based on the ultrasound signals to determine a display result and displaying the display result, for example, as an angiogram. An ultrasound medical diagnostic imaging device includes an ultrasound transducer for receiving a first and second (in general, N) ultrasound signal reflections from a target. Each ultrasound signal reflection is preferably oriented at a different angle. The device further includes a processor coupled to the ultrasound transducer for evaluating a display decision algorithm based on the ultrasound signals to determine a display result. A display coupled to the processor shows the display results, for example, as an angiogram.

24 Claims, 3 Drawing Sheets

METHOD AND APPARATUS FOR MULTIPLE ANGLE COMPOUND FLOW IMAGING

BACKGROUND OF THE INVENTION

Medical diagnostic ultrasound devices today play a crucial role in patient examination and diagnosis. The most common modes of diagnostic ultrasound imaging include B and M modes (used to image internal structures), Doppler, and color flow (the latter two used primarily to image flow characteristics, such as blood flow in blood vessels). In conventional B mode imaging, an ultrasound scanner transmits ultrasound signals into the body over a range of angles and focused at a desired depth. The ultrasound scanner creates images in which the brightness of a pixel corresponding to an angle and depth is based on the intensity or strength of ultrasound signal reflections from internal structure.

The color flow mode reveals the velocity of blood flow toward or away from the transducer, as determined by the measured frequency shift between transmitted and received ultrasound signals. Blood flow toward the transducer results in a higher frequency ultrasound signal reflection, while blood flow away from the transducer results in a lower frequency ultrasound signal reflection (measured at the transducer). The magnitude of the frequency shift is related to the velocity of blood flow. The frequency shift measurement techniques are also the basis of Doppler mode. However, whereas Doppler mode displays velocity versus time for a single selected sample volume, color flow mode displays hundreds of adjacent sample volumes simultaneously, all superimposed on a B-mode image and color-coded to represent velocity in each sample volume.

In the past, however, measured flow velocity has been obtainable more easily from larger vessels that carry fluid flow primarily in one direction (such as those found in the arms and legs). In part, this limitation stems from the fact that frequency shift (i.e., Doppler shift) is an angle dependent phenomenon. In other words, frequency shift varies from substantially zero when the transmitted ultrasound signal is incident normal to blood flow, to a maximum when the transmitted ultrasound signal is incident parallel to blood flow. The limitation also stems from the fact that smaller vessels are often blocked (or acoustically shadowed) by larger objects in the body, particularly from certain angles. Thus, regions of the body with many small blood vessels often suffered from poor imaging.

Some areas of the body have high blood vessel density (and thus have blood vessels oriented at many angles) or include blood vessels branch that branch in many directions. These areas often present near normal angles of incidence to transmitted ultrasound signals. As noted above, near normal angles of incidence reduce frequency shift between transmitted and reflected ultrasound signals to near zero. Thus, the ultrasound signal reflections contain little information about fluid flow in such areas of the body, thereby preventing accurate colorflow and Doppler imaging of the area.

Thus, a need has long existed for an improved method and apparatus for ultrasound imaging which overcomes the difficulties noted above, and others previously experienced.

BRIEF SUMMARY OF THE INVENTION

A method is provided for multi-angle compound flow imaging that includes the steps of receiving at an ultrasound transducer first and second (in general, N) ultrasound signal reflections from a target. The ultrasound signal reflections are oriented at a first and second angle with respect to an ultrasound transducer normal. The method then jointly evaluates information derived using the first and second ultrasound signal reflections to determine a display result for the target and displays the display result, for example, in an angiogram.

The joint evaluation may include determining a first velocity associated with blood flow in the target using the first ultrasound signal reflection, determining a second velocity associated with blood flow in the target using the second ultrasound signal reflection, and selecting the greater of the first and second velocity as the display result. Similarly, the joint evaluation may include determining a first velocity associated with blood flow in the target using the first ultrasound signal reflection, determining a second velocity associated with blood flow in the target using the second ultrasound signal reflection; and assigning the average of the first and second velocity as the display result. Alternatively, the joint evaluation may select one of the first ultrasound signal reflection and the second ultrasound signal reflection as a greatest energy ultrasound signal reflection and set as the display result blood flow velocity information derived using the greatest energy ultrasound signal reflection. The foregoing are examples only however, and other joint evaluations of the received ultrasound signals may also be used.

An apparatus for ultrasound imaging device is provided that includes an ultrasound transducer for receiving first and second ultrasound signal reflections from a target. The first and second ultrasound signal reflections are oriented at first and second angles with respect to an ultrasound transducer normal. A processor is coupled to the ultrasound transducer and jointly evaluates information derived using the first and second ultrasound signal reflections to determine a display result for the target. A display coupled to the processor for displays the display result, for example, in a colorflow mode, Doppler mode, or angiogram.

The processor may, for example, determine a first velocity associated with blood flow in the target using the first ultrasound signal reflection, determine a second velocity associated with blood flow in the target using the second ultrasound signal reflection, and select the greater of the first and second velocity as the display result. As another example, the processor, during the joint evaluation process, may determine a first velocity associated with blood flow in the target using the first ultrasound signal reflection, determine a second velocity associated with blood flow in the target using the second ultrasound signal reflection, and set the average of the first and second velocity as the display result. Alternatively, the processor may select one of the first and second signal reflections as a greatest energy ultrasound signal reflection and set as the display result blood flow velocity information derived using the greatest energy ultrasound signal reflection.

The method and apparatus may determine that the most accurate blood flow information, for example, consistently returns along a particular angle. That angle may be selected for a predetermined duration as the only angle along which blood flow velocity information is extracted from ultrasound signal reflections. Furthermore, the ultrasound signal reflections may result from individually transmitted ultrasound signals at numerous angles, or from a single centrally transmitted ultrasound signal.

The ultrasound imaging method and apparatus of the preferred embodiment provide an enhanced ability to accurately image fluid flow, particularly in those areas of the body that are dense with blood vessels (in comparison, for example, to an arm or leg). Thus, as examples, the kidneys, thyroid gland, brain, testes, breast, and even areas of Neo-Vascularization (including that cause by malignant tissue) may be visualized. The present techniques further allow selection between relatively higher frame rate, enhanced imaging in a lower frame rate examination mode (such as an angiography mode), or persistent reception of ultrasound signal reflections at selected angles that provide the most accurate fluid flow information.

DETAILED DESCRIPTION OF THE INVENTION

Figure 1:
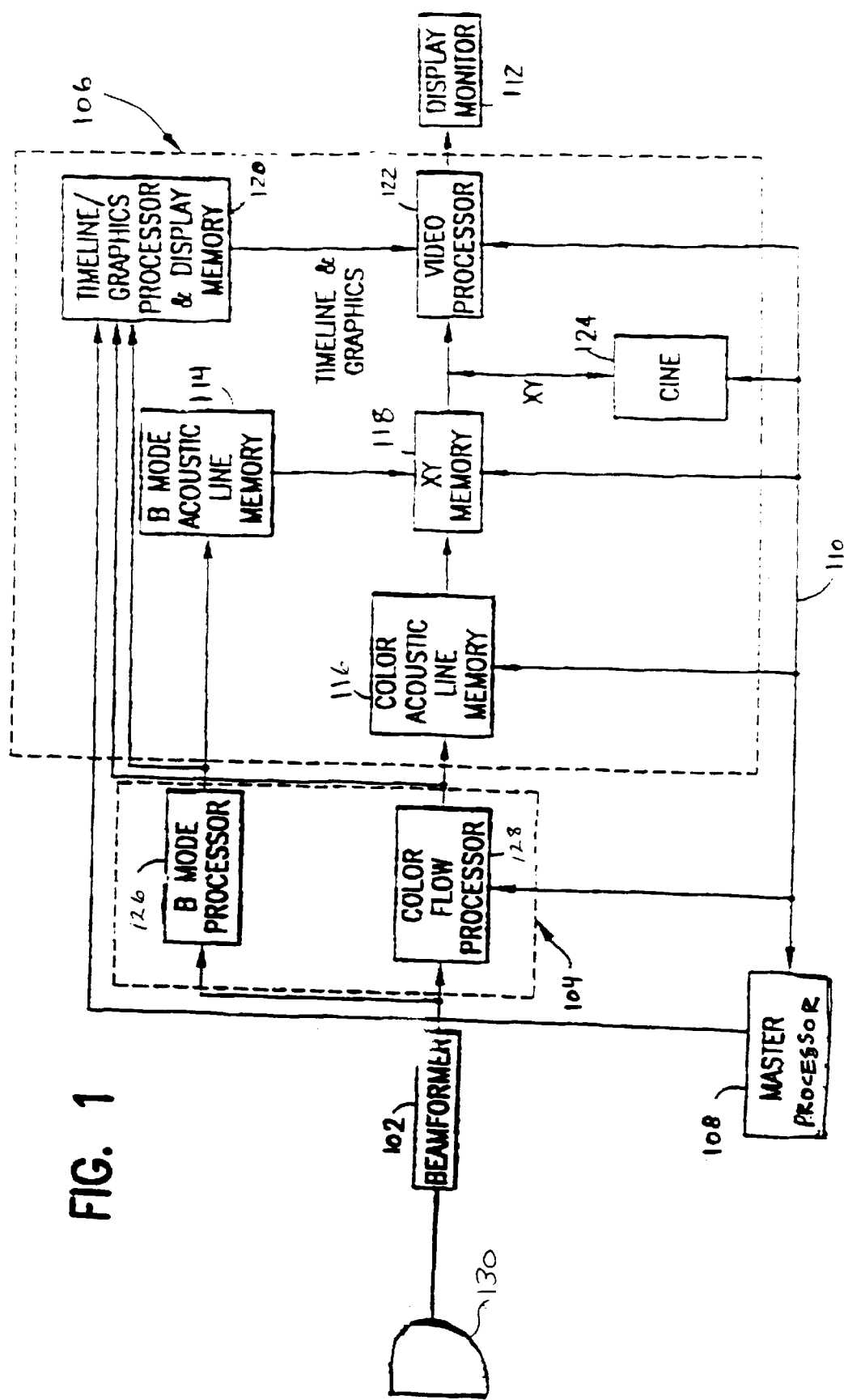
FIG. 1 illustrates a block diagram of an ultrasound imaging device.

Turning now to FIG. 1, that figure shows an example of an ultrasound imaging device 100 that may be used for B-mode, M-mode, Doppler, Colorflow (power or velocity), and angiographic imaging, as examples. The imaging device 100 includes a beamformer subsystem 102, a processor subsystem 104, a display converter 106, and a master processor 108. System control is centered in the master processor 108, which accepts operator inputs through an interface (not shown) and in turn controls the various subsystems including the B-mode processor 126 and the color flow processor 128. Alternatively, the imaging device 100 may be implemented with a single processor, for example, in a personal computer. The master processor 108 and other subsystems operate under control of timing and control signals distributed by a system control bus 110.

The beamformer subsystem 102 couples to the B-mode processor 126 and the color flow processor 128 where ultrasound beams (transmitted and received by the ultrasound transducer 130) are processed according to the acquisition mode and output as processed acoustic vector (beam) data to the display controller 106. The display controller 106 accepts the processed vector data and outputs the video display signals for the image in a raster scan format to a color monitor 112. The display controller 106, in cooperation with the master processor 108 also formats multiple images for display, handles display annotation, graphics overlays and replay of cine loops and recorded timeline data.

The frequency of ultrasound signal reflections returning from a target (e.g., a blood vessel) shifts in proportion to the velocity of fluid flow in the blood vessel. The color flow processor 128 provides a real-time two dimensional image of blood velocity in the imaging plane. The blood velocity may be determined by Doppler shift, or by evaluating the phase shift from transmission to transmission of ultrasound signals at one or more specific range gates.

The acoustic line memories 114 and 116 accept processed digital data from the B-mode processor 126 and the color flow processor 128. A coordinate transform of the color flow and B-mode data may then be applied to convert polar coordinates, sector format, or Cartesian coordinate data to appropriately scaled Cartesian coordinate display pixel data stored in the X-Y display memory 118. Graphics data for showing overlays on the displayed image may be stored in the display memory 120. Previously captured data may be stored in the cine memory 124, allowing the operator to view previous image data. The video processor 122 may then multiplex between the graphics data, image data, and time line data to generate the final video output in a raster scan format on the video monitor 112.

The master processor 108 operates as described below to enhance imaging of target areas that are densely packed with blood vessels and in which blood vessels branch in many directions.

Figure 2:
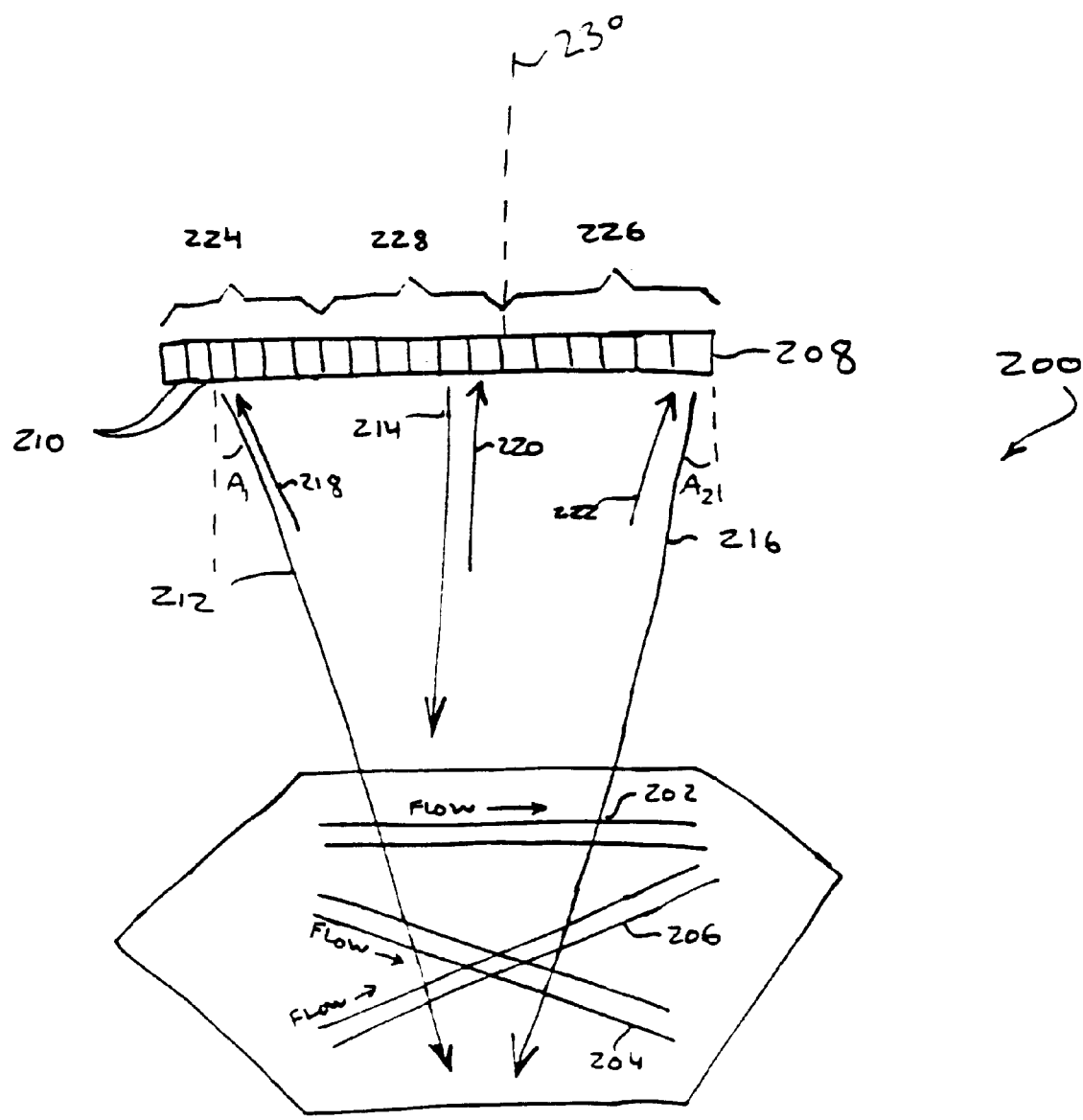
FIG. 2 shows an anatomical cross section subject to examination by multiple ultrasound signals at different angles.

Turning now to FIG. 2, that figure shows an anatomical cross section 200. The cross section 200 includes targets such as the first blood vessel 202, second blood vessel 204, and third blood vessel 206. Blood flow direction for the blood vessels 202–206 are illustrated by the associated arrows. A transducer 208 (formed, for example, from multiple transducer elements 210) examines the cross section 200 by transmitting ultrasound signals (e.g., left transmitted signal 212, central transmitted signal 214, and right transmitted signal 216) into the cross section 200 and receiving ultrasound signal reflections (e.g., left signal reflection 218, central signal reflection 220, and right signal reflection 222) in return. The transducer 208 is divided for illustration purposes into sections: a first section 224, a second section 226, and a third section 228. The transducer 208, however, may transmit or receive using any portion of the transducer 208 (including the whole transducer 208). Furthermore, the transducer 208 may be used to transmit and receive ultrasound signals along one line, transmit along one line and receive along multiple lines, or transmit along multiple lines and receive along multiple lines.

The transmitted and received reflected signals 212, 218 are oriented at angle $A_1$ with respect to the transducer normal 230, while transmitted and received reflected signals 216, 222 are oriented at angle $A_2$. Although three transmitted and reflected signals are shown in FIG. 2, there may be, in general, N transmitted and reflected signals, each oriented at a different angle with respect to the transducer normal 230. As will be explained in more detail below, the left, central, and right transmitted signals 212–216 are generally produced to image a point for display, and may result from a single firing or multiple sequential firings. Many individual points may then be imaged and displayed to produce, for example, an angiogram.

As noted briefly above, the frequency shift (i.e., the Doppler shift) between a signal transmitted to a target and a signal reflection received from that target varies according to the angle of incidence of the transmitted signal with respect to the motion of the target. Frequency shift is substantially zero when the transmitted ultrasound signal is incident normal to the direction of motion of the target. Frequency shift increases to a maximum when the transmitted ultrasound signal is incident parallel to motion of the target. The most accurate indication of target velocity occurs when the frequency shift is maximum.

Still with reference to FIG. 2, note that the blood vessel 202 is oriented parallel to the transducer 208. Thus, the left and right transmitted signals 212 and 216 return with approximately the frequency shift (though in opposite directions), and therefore, when analyzed, yield approximately the same fluid flow velocity. The central signal 214 returns with approximately zero velocity (and therefore, when analyzed, yields approximately zero fluid flow velocity). With regard to the blood vessel 204, analysis of the left transmitted signal 212 returns a relatively large velocity, analysis of the central transmitted signal 214 returns a relatively small velocity, and analysis of the right transmitted signal 216 returns approximately zero velocity. Similarly, with regard to the blood vessel 206, the analysis of the left transmitted signal 212 returns approximately zero velocity, analysis of the central transmitted signal 214 returns a relatively small velocity, and analysis of the right transmitted signal 216 returns a relatively large velocity. As a result, the left and right signal reflections 218 and 222 return the most accurate blood flow information for the blood vessel 202, the left signal reflection 218 returns the most accurate blood flow information for the blood vessel 204, and the right signal reflection 222 returns the most accurate blood flow information for the blood vessel 206.

During examination, to find the most accurate fluid flow information for a display point, one examination technique uses the beamformer subsystem 102 to create a transmitted ultrasound signal at a certain angle, and receive a signal reflection from that angle. Transmission and reception may repeat at any number, N, of symmetric or non-symmetric angles. As one example, left transmitted signal 212 may be oriented at −15 degrees from normal to the transducer 208, while the right transmitted signal 216 may be oriented +15 degrees from normal to the transducer 208. Additional transmitted signals may originate from any desired direction using the beamforming subsystem 102 (e.g., +5 degrees, −7 degrees, 0 degrees, +10 degrees, −20 degrees, and the like). As explained in more detail below, a display decision algorithm determines a display result from the information returned by the signal reflections. Numerous display results may be used to form, for example, an angiogram or color-flow image.

An alternate examination mode with a generally higher frame rate entails transmitting a single ultrasound signal, for example the central transmitted signal 214, toward a target. Because tissue dense with blood vessels (such as the Thyroid or Kidney), and areas of Neo-Vascularization tend to scatter the transmitted ultrasound signal in many directions, a single transmitted signal will in general generate reflections oriented at many angles. Such scattering results from the close proximity of large numbers of blood vessels (and their branches) oriented at many different angles, with each of the different blood vessel orientations reflecting signal energy at a different angle. The beamforming subsystem 102 may then receive from multiple angles simultaneously, for example, using the transducer sections 224-228. In other words, each transducer section 224-228 may operate as an independent ultrasound transducer (smaller than the full transducer 208), serving to receive (or transmit) signals using the transducer elements that make up the transducer section 224-228 in question.

After receiving ultrasound signal reflections from multiple preferably symmetric angles (e.g., −10 degrees, +10 degrees, −25 degrees, +25 degrees with respect to a transducer 208 normal) reflected from a target, the master processor 108 evaluates a display decision algorithm (illustrated in more detail in FIG. 3) to determine a display result based on the signal reflections. As one example, the master processor 108 may determine velocities associated with blood flow in the target from each of the ultrasound signal reflections 218-222, and select the greatest velocity as the display result. Thus, for example, in evaluating the reflected ultrasound signals 218-222 when imaging the blood vessel 204, the left ultrasound signal reflection 218 is found to carry the most accurate information about blood flow velocity. The blood flow velocity information extracted from the reflected ultrasound signal 218 is therefore used as a display result.

As another example, the master processor 108 may select as the display result the average of the velocities. In yet another embodiment, the master processor 108 may determine the energies in the ultrasound signal reflections 218-222 and select as the display result that information (flow velocity and the like) derived using the reflected signal with the greatest energy.

By tracking the angles at which reflected ultrasound signal reflections show the greatest frequency shift, for example, the master processor 108 may determine that ultrasound signal reflections returning along a particular angle (or to a particular ultrasound transducer 208 section 224-228) consistently carry the most accurate blood flow velocity information. As noted above, for example, when imaging the blood vessel 204, the left ultrasound signal reflection 218 carries the most accurate information about blood flow velocity. The master processor 108 may then elect to receive ultrasound signal reflections only from angle $A_1$, only for a predetermined duration. For example, the master processor 108 may receive ultrasound signal reflections only from angle $A_1$ for the duration of the examination procedure, for a predetermined number of seconds, or for a predetermined number of ultrasound signal transmissions (firings). After the predetermined duration has elapsed, the master processor 108 may again transmit and receive ultrasound signals from numerous angles to determine whether flow direction or velocity has shifted, and to determine whether a different reception angle consistently returns the most accurate blood flow velocity information.

Figure 3:
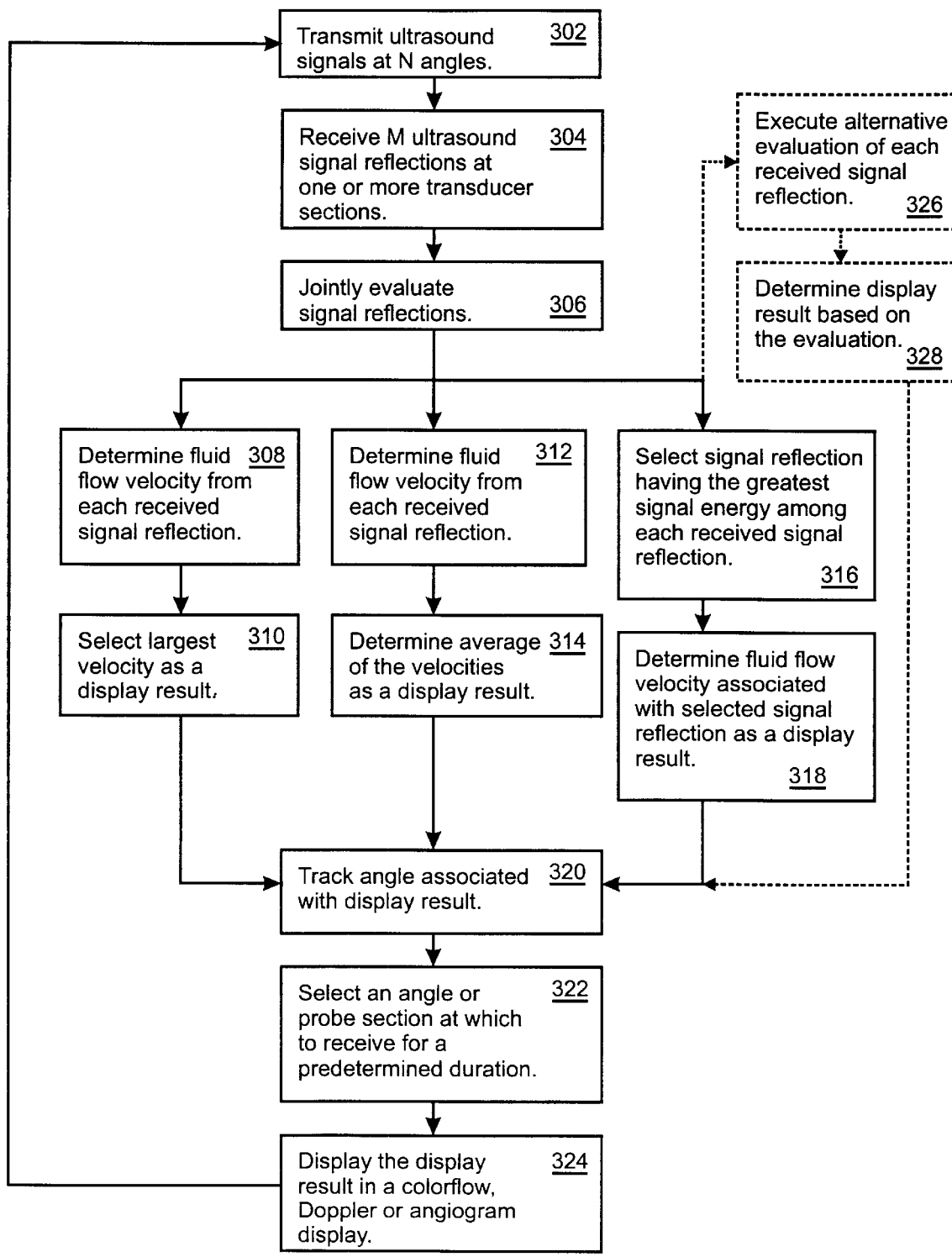
FIG. 3 shows a flow diagram of a technique for multi-angle compound flow imaging.

Turning now to FIG. 3, that figure shows a flow diagram 300 of the processing steps occurring in the imaging device 100. At step 302, the imaging device transmits N ultrasound signals (for example, symmetric with respect to the transducer normal 230) or a single centered ultrasound signal into a region of interest containing a target to be imaged. At step 304, the imaging device 100 receives M ultrasound signal reflections (where M is not necessarily equal to N) returned from the target at one or more sections of an ultrasound transducer sequentially or simultaneously. The imaging device 100 then executes a display decision algorithm that jointly evaluates the ultrasound signal reflections to select a display result. In other words, characteristics of, or information derived from each ultrasound signal reflection is preferably considered among all the ultrasound signal reflections to determine a single display result. FIG. 3 illustrates three possibilities that were explained in detail above. The present technique, however, is not limited to the following examples, but may be used in connection with other joint evaluations of the received ultrasound signals.

One alternative is to determine fluid flow velocity from each received signal reflection (step 308), then select the largest velocity as a display result (step 310). A second alternative is to determine fluid flow velocity from each received signal reflection (step 312), then determine the average of the velocities as a display result (step 314). A third possibility is to select a signal reflection having the greatest signal energy among each received signal reflection (step 316), then determine as a display result the blood flow velocity associated with the selected signal reflection (step 318). The angle associated with the display result (i.e., the angle along which a signal reflection returns from which a display result is determined) is tracked at step 320.

Thus, as noted above, the master processor 108 may continue to transmit and receive ultrasound signals only along a selected angle (e.g., angle $A_1$, in the example above) using one or more sections of the ultrasound transducer, or the whole transducer (step 322) for a predetermined amount of time. Steps 320 and 322 are optional and therefore processing may instead continue at step 324. At step 324, the display result returned from the display decision algorithm is presented on a display, for example, in colorflow mode, Doppler mode, or as part of an angiogram. Processing repeats at step 302.

As noted above, the maximum velocity, energy, and average velocity joint evaluations of the received ultrasound signals are examples only. Thus, at step 326 any desired alternative evaluation of the received ultrasound signals may be performed. Correspondingly, at step 328, the display result is based upon the alternative evaluation for display.

An example frame rate calculation is presented below for the case in which two ultrasound signals are individually transmitted and received at two different angles in a multi line acquisition (MLA) mode to determine display results:

Depth=6 cm; Signal propagation delay=1.3 us;
Quality=12; Compound=2;
Angio lines=40; MLA returns 2 lines per firing.
2D lines=128; MLA returns 2 lines per firing.

$$\text{Frame rate} = 1/(\text{Compound} * ((2D \text{ lines}/MLA) +$$
$$(\text{Quality} * \text{Angio lines}/MLA)) * \text{depth} * 1.3 us)$$
$$= 1/(2*(64+240)*60*1.3e-6)$$
$$= 21.1 \text{ Hz.}$$

The multiple angle compound flow imaging techniques of the preferred embodiment provide enhanced imaging of fluid flow in previously hard to image areas of the body (e.g., areas with a relatively high concentration of blood vessels in comparison, for example, to an arm or leg). Thus, the kidneys, thyroid gland, brain, breast, testes, and even areas of Neo-Vascularization may be visualized. The present techniques further provide multiple options for evaluating the ultrasound signal reflections returned, thereby allowing an operator to achieve a high frame rate, enhanced imaging in a lower frame rate examination mode (such as an angiography mode), or reception of ultrasound signal reflections at selected angles that provide the most accurate fluid flow information.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In an ultrasound imaging device, a method for multi-angle compound flow imaging comprising:
   receiving at an ultrasound transducer a first ultrasound signal reflection from a target, the first ultrasound signal reflection being oriented at a first angle with respect to an ultrasound transducer normal;
   receiving at an ultrasound transducer a second ultrasound signal reflection from the target, the second ultrasound signal reflection being oriented at a second angle with respect to the ultrasound transducer normal;
   jointly evaluating information in the first and second ultrasound signal reflections, selecting one of the first and second ultrasound signal reflections based on a result of the jointly evaluating step; and
   displaying the selected one of the first and second ultrasound signal reflections as a display result for a target.

2. The method of claim 1, wherein the evaluating step comprises:
   determining a first velocity associated with blood flow in the target using the first ultrasound signal reflection;
   determining a second velocity associated with blood flow in the target using the second ultrasound signal reflection; and
   selecting the greater of the first and second velocity as the display result.

3. The method of claim 2, wherein the step of displaying comprises displaying an angiogram using a plurality of display results.

4. The method of claim 1, wherein the evaluating step comprises:
   determining a first velocity associated with blood flow in the target using the first ultrasound signal reflection;
   determining a second velocity associated with blood flow in the target using the second ultrasound signal reflection; and
   assigning the average of the first and second velocity as the display result.

5. The method of claim 1, wherein the selecting step comprises:
   selecting the one of the first ultrasound signal reflection and the second ultrasound signal reflection having the greatest energy ultrasound signal reflection.

6. The method of claim 1, further comprising the step of:
   receiving a plurality of additional ultrasound signal reflections from the target at a plurality of additional angles;
   and wherein the jointly evaluating and selecting steps use the first, second, and additional ultrasound signal reflections to determine the display result for the target.

7. The method of claim 6, wherein the evaluating step comprises:
   determining a first velocity associated with blood flow in the target using the first ultrasound signal reflection;
   determining a second velocity associated with blood flow in the target using the second ultrasound signal reflection;
   determining a plurality of additional velocities associated with blood flow in the target using the plurality of additional ultrasound signal reflections; and
   selecting the greatest of the first, second, and additional velocities as the display result.

8. The method of claim 6, wherein the evaluating step comprises:
   determining a first velocity associated with blood flow in the target using the first ultrasound signal reflection;
   determining a second velocity associated with blood flow in the target using the second ultrasound signal reflection;
   determining a plurality of additional velocities associated with blood flow in the target using the plurality of additional ultrasound signal reflections; and
   setting the average of the first, second, and additional velocities to the display result.

9. The method of claim 6, wherein the selecting step comprises:
   selecting one of the first ultrasound signal reflection, the second ultrasound signal reflection, and the additional ultrasound signal reflections as a greatest energy ultrasound signal reflection.

10. An ultrasound imaging device comprising:
an ultrasound transducer for receiving a first ultrasound signal reflection from a target, the first ultrasound signal reflection being oriented at a first angle with respect to an ultrasound transducer normal, and for receiving a second ultrasound signal reflection from the target, the second ultrasound signal reflection being oriented at a second angle with respect to the ultrasound transducer normal;
a processor coupled to the ultrasound transducer for jointly evaluating information in the first and second ultrasound signal reflections and selecting one of the first and second ultrasound signal reflections based on a result of the jointly evaluated information to determine a display result for a target; and
a display coupled to the processor for displaying the display result.

11. The imaging device of claim 10, wherein the processor determines a first velocity associated with blood flow in the target using the first ultrasound signal reflection, determines a second velocity associated with blood flow in the target using the second ultrasound signal reflection, and selects the greater of the first and second velocity as the display result.

12. The imaging device of claim 10, wherein the processor determines a first velocity associated with blood flow in the target using the first ultrasound signal reflection, determines a second velocity associated with blood flow in the target using the second ultrasound signal reflection, and sets the average of the first and second velocity to the display result.

13. The imaging device of claim 10, wherein the processor determines selects one of the first ultrasound signal reflection and the second ultrasound signal reflection as a greatest energy ultrasound signal reflection; and sets as the display result blood flow velocity information derived using the greatest energy ultrasound signal reflection.

14. The imaging device of claim 10, wherein the target is an internal structure having a relatively high concentration of small blood vessels.

15. The imaging device of claim 14, wherein the target is one of a Kidney, Thyroid gland, brain, breast, testes, or area of Neo-Vascularization.

16. The imaging device of claim 10, wherein the display displays an angiogram using a plurality of the display results.

17. An ultrasound imaging device comprising:
an ultrasound transducer for receiving a first ultrasound signal reflection from a target, the first ultrasound signal reflection being oriented at a first angle with respect to an ultrasound transducer normal, and for receiving a second ultrasound signal reflection from the target, the second ultrasound signal reflection being oriented at a second angle with respect to the ultrasound transducer normal;
a processor coupled to the ultrasound transducer for jointly evaluating information in the first and second ultrasound signals and selecting one of the first and second ultrasound signal reflections based on a result of the jointly evaluated information to determine a display result;
the processor controlling the ultrasound transducer to fire a transmit ultrasound signal from the ultrasound transducer, and to receive the first and second ultrasound signal reflections at the ultrasound transducer in response to the transmit ultrasound signal; and
a display coupled to the processor for displaying the display result.

18. The ultrasound medical diagnostic imaging device of claim 17, wherein the processor receives the first ultrasound signal on a first section of the ultrasound transducer and simultaneously receives the second ultrasound signal on a second section of the ultrasound transducer as a result of a single firing of the transmit ultrasound signal.

19. The ultrasound medical diagnostic imaging device of claim 17, wherein the processor controls the ultrasound transducer to transmit a plurality of transmit ultrasound signals in order to receive the first and second ultrasound signal reflections.

20. The imaging device of claim 17, wherein the decision algorithm determines a first velocity associated with blood flow in the target using the first ultrasound signal reflection, determines a second velocity associated with blood flow in the target using the second ultrasound signal reflection, and selects the greater of the first and second velocity as the display result.

21. The imaging device of claim 17, wherein the decision algorithm determines a first velocity associated with blood flow in the target using the first ultrasound signal reflection, determines a second velocity associated with blood flow in the target using the second ultrasound signal reflection, and sets the average of the first and second velocity to the display result.

22. The imaging device of claim 17, wherein the decision algorithm selects one of the first ultrasound signal reflection and the second ultrasound signal reflection as a greatest energy ultrasound signal reflection and sets as the display result blood flow velocity information derived using the greatest energy ultrasound signal reflection.

23. In an ultrasound imaging device, a method for multi-angle compound flow imaging comprising:
receiving at an ultrasound transducer a first ultrasound signal reflection from a target, the first ultrasound signal reflection being oriented at a first angle with respect to an ultrasound transducer normal;
receiving at an ultrasound transducer a second ultrasound signal reflection from the target, the second ultrasound signal reflection being oriented at a second angle with respect to the ultrasound transducer normal;
receiving a plurality of additional ultrasound signal reflections from the target at a plurality of additional angles;
jointly evaluating information derived using the first and second and additional ultrasound signal reflections to determine a display result for the target; and
displaying the display result.

24. An ultrasound imaging device comprising:
an ultrasound transducer for receiving a first ultrasound signal reflection from a target, the first ultrasound signal reflection being oriented at a first angle with respect to an ultrasound transducer normal, and for receiving a second ultrasound signal reflection from the target, the second ultrasound signal reflection being oriented at a second angle with respect to the ultrasound transducer normal, and for receiving a plurality of additional ultrasound signal reflections from the target at a plurality of additional angles;
a processor coupled to the ultrasound transducer for jointly evaluating information derived using the first and second and additional ultrasound signal reflections to determine a display result for the target; and
a display coupled to the processor for displaying the display result.

* * * * *